(12) United States Patent
Otsuki et al.

(10) Patent No.: US 11,232,863 B2
(45) Date of Patent: Jan. 25, 2022

(54) MEDICAL INFORMATION SYSTEM, MEDICAL APPARATUS, METHOD, AND NON-TRANSITORY COMPUTER READABLE MEDIUM

(71) Applicant: TOYOTA JIDOSHA KABUSHIKI KAISHA, Toyota (JP)

(72) Inventors: Nobuhisa Otsuki, Toyota (JP); Masayoshi Tsuchinaga, Nisshin (JP); Hodaka Kito, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/194,681

(22) Filed: Nov. 19, 2018

(65) Prior Publication Data
US 2019/0164645 A1 May 30, 2019

(30) Foreign Application Priority Data

Nov. 24, 2017 (JP) ............................. JP2017-226267

(51) Int. Cl.
*G16H 40/67* (2018.01)
*G16H 40/40* (2018.01)
(Continued)

(52) U.S. Cl.
CPC ............. *G16H 40/67* (2018.01); *G16H 40/40* (2018.01); *H04L 67/1097* (2013.01); *H04L 67/42* (2013.01)

(58) Field of Classification Search
CPC ........ G16H 40/67; G16H 40/40; H04L 67/42; H04L 67/1097
See application file for complete search history.

(56) References Cited

U.S. PATENT DOCUMENTS 9,021,161 B2* 4/2015 Vlach ................... G06F 3/0655
710/63
9,129,283 B1* 9/2015 Raju ................... G06Q 20/3829
(Continued)

FOREIGN PATENT DOCUMENTS

CN 106341244 A * 7/2015
CN 106341244 A * 1/2017
(Continued)

OTHER PUBLICATIONS

Microsoft 365 security, Access Control Overview (Windows 10)—Microsoft 365 Security | Microsoft Docs, Jul. 2017 (Year: 2017).*
(Continued)

*Primary Examiner* — John A Follansbee
*Assistant Examiner* — Fadi Haj Said
(74) *Attorney, Agent, or Firm* — Oblon, McClelland, Maier & Neustadt, L.L.P.

(57) ABSTRACT

The communication control unit of the external communication apparatus requests a communication connection to the server. When a communication connection with the server is established, the communication control unit acquires the server side definition file from the server. The updating unit of the external communication apparatus updates the client side definition file with the server side definition file acquired by the communication control unit. The communication control unit of the external communication apparatus is configured to upload the medical apparatus side data to the server based on the client side definition file. Further, the communication control unit of the external communication apparatus is configured to reject a connection request from the server.

7 Claims, 7 Drawing Sheets

(51) Int. Cl.
*H04L 29/08* (2006.01)
*H04L 29/06* (2006.01)

(56) References Cited

U.S. PATENT DOCUMENTS

| | | | |
|---|---|---|---|
| 9,411,610 B2* | 8/2016 | Urakawa | G06F 9/452 |
| 9,883,543 B2* | 1/2018 | Maheshwari | H04W 4/08 |
| 9,999,013 B2* | 6/2018 | Cacioppo | G09B 7/02 |
| 2003/0055741 A1 | 3/2003 | Yamamoto | |
| 2004/0069311 A1* | 4/2004 | Sasaki | G06F 19/321 |
| | | | 128/897 |
| 2005/0055242 A1 | 3/2005 | Bello et al. | |
| 2007/0179815 A1* | 8/2007 | Vining | G06F 19/3418 |
| | | | 705/3 |
| 2007/0282634 A1* | 12/2007 | Johnson | G16H 40/67 |
| | | | 705/3 |
| 2009/0177249 A1* | 7/2009 | Roberts | G16H 40/40 |
| | | | 607/60 |
| 2009/0254664 A1* | 10/2009 | Wada | H04L 67/14 |
| | | | 709/227 |
| 2011/0167133 A1* | 7/2011 | Jain | H04L 67/12 |
| | | | 709/219 |
| 2012/0182939 A1* | 7/2012 | Rajan | A61B 5/0008 |
| | | | 370/328 |
| 2013/0162160 A1 | 6/2013 | Ganton et al. | |
| 2013/0208966 A1* | 8/2013 | Zhao | G06F 9/5072 |
| | | | 382/131 |
| 2013/0339317 A1* | 12/2013 | Kim | G06F 16/1748 |
| | | | 707/692 |
| 2014/0059118 A1* | 2/2014 | Pidady | H04L 67/06 |
| | | | 709/203 |
| 2014/0142984 A1* | 5/2014 | Wright | G06F 19/321 |
| | | | 705/3 |
| 2016/0203264 A1* | 7/2016 | Danner | G06F 19/321 |
| | | | 382/128 |
| 2018/0013825 A1* | 1/2018 | Klose | G06F 16/119 |
| 2018/0241758 A1* | 8/2018 | Inoue | G06F 21/60 |
| 2018/0342314 A1* | 11/2018 | Tichy | G16H 30/20 |

FOREIGN PATENT DOCUMENTS

| | | | |
|---|---|---|---|
| JP | 2008-73456 A | | 4/2008 |
| JP | 2008-221600 A | | 9/2008 |
| JP | 2012208737 A | * | 10/2012 |
| JP | 6097313 | | 3/2017 |
| JP | 2017-143992 A | | 8/2017 |
| JP | 6187208 | | 8/2017 |

OTHER PUBLICATIONS

Anonymous: "Personal firewall", Wikipedia, XP055570541, Jun. 25, 2017, pp. 1-3.

* cited by examiner

| DEFINITION FILE ||| 
|---|---|---|
| UPLOAD TIME || 3:00 |
| UPLOAD TIME INTERVAL || — |
| CORRESPONDING DATA | SYSTEM OPERATING STATE | NO |
| | SYSTEM ERROR MESSAGE | NO |
| | SENSOR DATA | NO |
| | OS OPERATION LOG | NO |
| | TRAINING DATA | YES |
| | SYSTEM BACKUP | NO |
| FILE DIVISION | NUMBER OF DIVISIONS | 127 |
| | DIVISION SIZE | — |
| COMPRESSION REQUIRED || YES |
| TRAINEE DATA ANONYMIZATION REQUIRED || NO |
| TRAINING DATA ENCRYPTION REQUIRED || YES |
| ENCRYPTION KEY INFORMATION || ******** |
| DEFINITION FILE UPDATE TIME || 4:00 |

MEDICAL INFORMATION SYSTEM, MEDICAL APPARATUS, METHOD, AND NON-TRANSITORY COMPUTER READABLE MEDIUM

CROSS REFERENCE TO RELATED APPLICATIONS

This application is based upon and claims the benefit of priority from Japanese patent application No. 2017-226267, filed on Nov. 24, 2017, the disclosure of which is incorporated herein in its entirety by reference.

BACKGROUND

The present disclosure relates to a medical information system, a medical apparatus, a data communication method, and a program.

Patent Literature 1 (Japanese Patent No. 6187208) discloses a walking rehabilitation system that trains a hemiplegic patient suffering from paralysis in one of his/her legs to walk.

SUMMARY

Incidentally, when medical apparatus side data held by a medical apparatus is uploaded to a server to collectively manage medical apparatus side data, it is preferable that the medical apparatus hold a definition file that defines a mode of the uploading, and a server side is permitted to freely update the definition file.

However, when the server side is permitted to freely update the definition file, for example, the definition file held by the medical apparatus may be rewritten by an external server different from an authorized server without a permission, which poses a problem in terms of security.

An object of the present disclosure is to provide a technique for permitting the authorized server to freely update the definition file and prohibiting the external server other than the authorized server from updating the definition file.

The present disclosure provides a medical information system including: a server; and a medical apparatus configured to upload medical apparatus side data to the server. The server includes a server side definition file storage unit configured to store a server side definition file that defines a mode of the uploading. The medical apparatus includes: a medical apparatus side data storage unit configured to store the medical apparatus side data; a client side definition file storage unit configured to store a client side definition file that defines the mode of the uploading; a communication control unit configured to control communication with the server; and an updating unit configured to update the client side definition file. The communication control unit of the medical apparatus requests a communication connection to the server, and when the communication connection is established with the server, the communication control unit acquires the server side definition file from the server. The updating unit of the medical apparatus updates the client side definition file with the server side definition file acquired by the communication control unit. The communication control unit of the medical apparatus is configured to upload the medical apparatus side data to the server based on the client side definition file. The communication control unit is configured to reject a connection request from the server. With the above configuration, the definition file can be freely updated by an authorized server, and the definition file can be prohibited from being updated by an external server other than the authorized server.

Preferably, the medical apparatus side data includes medical data of a subject of the medical apparatus. With the above configuration, the medical data is effectively prevented from leaking.

Preferably, the client side definition file defines at least one of a time for executing the uploading, a time interval for executing the uploading, and a type of data to be uploaded. With the above configuration, the client side definition file specifically defining the mode of the uploading is achieved.

The present disclosure further provides a medical apparatus for uploading medical apparatus side data to a server based on a definition file that defines a mode of the uploading. The medical apparatus includes: a medical apparatus side data storage unit configured to store the medical apparatus side data; a definition file storage unit configured to store the definition file; a communication control unit configured to control communication with the server; and an updating unit configured to update the definition file. The communication control unit requests a communication connection to the server, and when the communication connection is established with the server, the communication control unit acquires the definition file stored in the server. The updating unit updates the definition file stored in the definition file storage unit with the definition file acquired by the communication control unit. The communication control unit is configured to upload the medical apparatus side data to the server based on the definition file. The communication control unit is configured to reject a connection request from the server. With the above configuration, the definition file can be freely updated by an authorized server, and the definition file can be prohibited from being updated by an external server other than the authorized server.

The present disclosure still further provides a data communication method of a medical apparatus in which the medical apparatus uploads medical apparatus side data to a server based on a definition file that defines a mode of the uploading. The data communication method includes: requesting, by the medical apparatus, a communication connection to the server, and when the communication connection is established with the server, acquiring, by the medical apparatus, the definition file stored in the server; updating, by the medical apparatus, the definition file stored in the medical apparatus with the acquired definition file; and uploading, by the medical apparatus, the medical apparatus side data to the server based on the definition file stored in the medical apparatus. The medical apparatus rejects a connection request from the server. With the above method, the definition file can be freely updated by an authorized server, and the definition file can be prohibited from being updated by an external server other than the authorized server.

A program for causing a computer to execute the above-described data communication method is provided.

According to the present disclosure, the definition file can be freely updated by an authorized server, and the definition file can be prohibited from being updated by an external server other than the authorized server.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, although the present disclosure will be described with reference to an embodiment of the invention, the present disclosure according to claims is not limited to the following embodiment. Further, all the components described in the following embodiment are not necessarily indispensable for means to solve problems.

Figure 1:
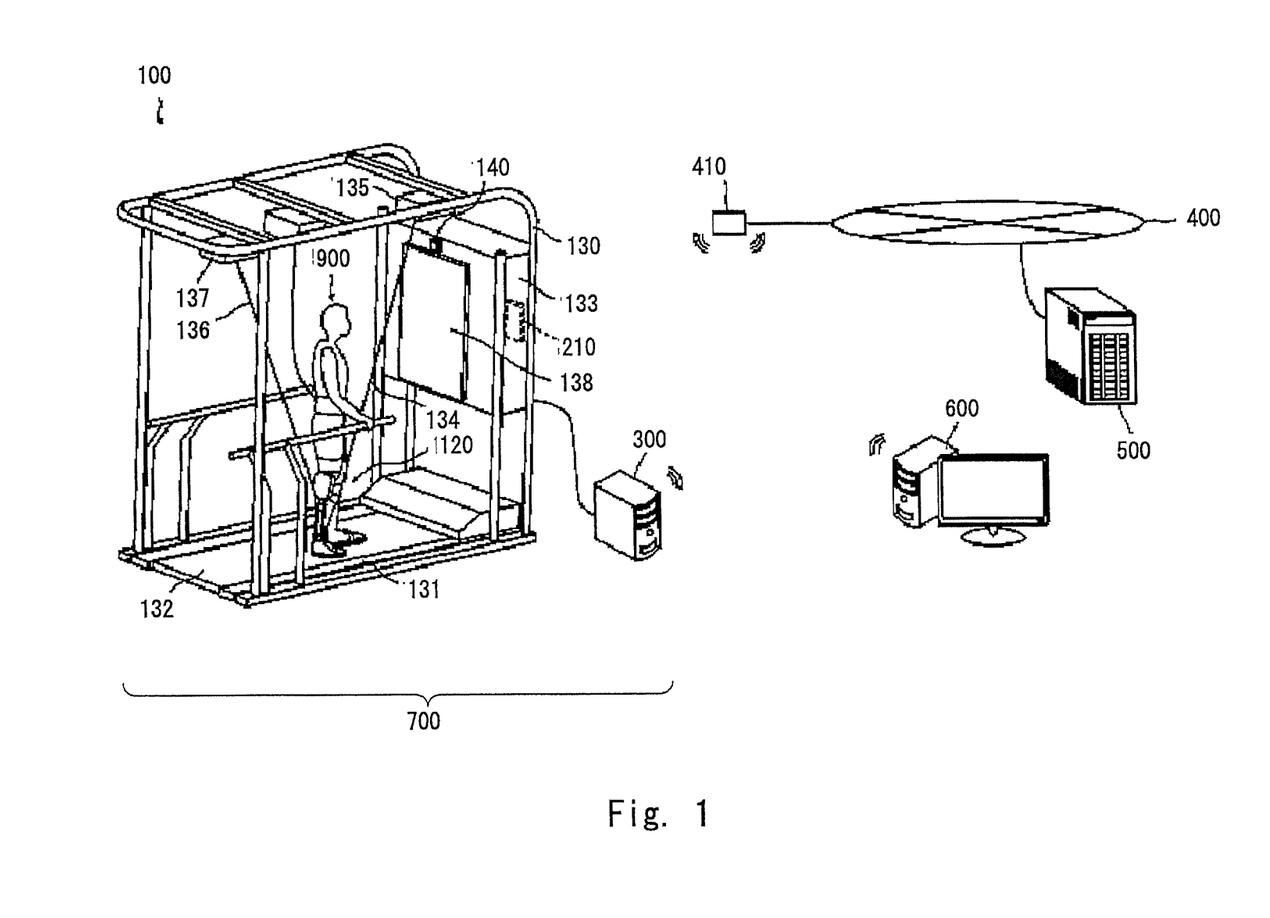
FIG. 1 is an overall conceptual diagram of a walking training system according to this embodiment.

FIG. 1 is an overall conceptual diagram showing a walking training system according to this embodiment. The walking training system mainly includes a walking training apparatus 100, an external communication apparatus 300 and a server 500. The walking training apparatus 100 is an apparatus by which a trainee 900, who is, for example, a hemiplegia patient suffering from paralysis in one of his/her legs, does walking training. The walking training apparatus 100 outputs training data generated by associating a training result of the trainee 900 with information attributed to the trainee 900, such as the name of the trainee 900. The trainee 900 is a subject and the training data of the trainee 900 is handled as medical data showing a status of rehabilitation of the subject. The walking training apparatus 100 and the external communication apparatus 300 constitute a medical apparatus 700. The walking training apparatus 100 and the external communication apparatus 300 are physically separate apparatuses in this embodiment. However, the walking training apparatus 100 and the external communication apparatus 300 may be integrated into one apparatus.

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900. The frame 130 is disposed on the treadmill 131 mounted on a floor surface in a standing state. The treadmill 131 makes an endless belt 132 run by a motor (not shown). The treadmill 131 is an apparatus which urges the trainee 900 to walk. The trainee 900, who is performing walking training, gets on the endless belt 132 and tries to walk according to the movement of the endless belt 132.

The frame 130 supports the control panel 133 that houses an overall control unit 210 that controls motors or sensors, a training monitor 138 that is formed by, for example, a liquid-crystal panel and shows progress of the training etc. to the trainee 900, and so on. Further, the frame 130 supports a front pulling unit 135 in a position located above and in front of the head of the trainee 900 and a rear pulling unit 137 in a position located above and behind the head of the trainee 900.

A camera 140 functions as an image pickup unit for observing the whole body of the trainee 900. The camera 140 is disposed in the vicinity of the training monitor 138 so that it faces the trainee. The camera 140 includes a set of a lens and an image pickup device having such an angle of view that the whole body of the trainee 900 can be captured. The image pickup device is, for example, a CMOS image sensor, and it converts an optical image formed on an image forming surface into an image signal.

One end of a front wire 134 is connected to a winding mechanism of the front pulling unit 135 and the other end of the front wire 134 is connected to the walking assistance apparatus 120. The winding mechanism of the front pulling unit 135 winds up and pays out the front wire 134 according to the movement of the diseased leg by turning on or off the motor (not shown). Similarly, one end of a rear wire 136 is connected to a winding mechanism of the rear pulling unit 137 and the other end of the rear wire 136 is connected to the walking assistance apparatus 120. The winding mechanism of the rear pulling unit 137 winds up and pays out the rear wire 136 according to the movement of the diseased leg by turning on or off the motor (not shown). By such cooperative operations performed by the front and the rear pulling units 135 and 137, the load (e.g., the weight) of the walking assistance apparatus 120 is cancelled out and hence does not act as a burden on the diseased leg, and a swinging motion of the diseased leg is assisted according to a set level.

For example, an operator who is a training assistant sets an assisting level to a high value for a trainee having severe paralysis. When the assisting level is set high, the front pulling unit 135 winds up the front wire 134 with a relatively strong force in synchronization with the swinging motion of the diseased leg. When the assistance becomes unnecessary as the training proceeds, the operator sets the assisting level to a minimum value. When the assisting level is set to the minimum value, the front pulling unit 135 winds up the front wire 134 with a force by which the weight of the walking assistance apparatus 120 is just cancelled in synchronization with the swinging motion of the diseased leg.

The walking assistance apparatus 120 is attached to the diseased leg of the trainee 900 to assist the trainee 900 in his/her walking by reducing the burden of extending and bending motions in the knee joint of the diseased leg. Specifically, the burden in the knee joint of the diseased leg is reduced by using the motor (not shown) which generates a driving force to assist the extending and bending motions of the knee joint. Further, the walking assistance apparatus 120 includes a sensor and the like for measuring a load (e.g., a pressure) on the sole, and outputs their outputs as data on the moving leg to the overall control unit 210.

The external communication apparatus 300 has a function of receiving and storing training data output from the walking training apparatus 100. Further, the external communication apparatus 300 has functions of transmitting the training data to the server 500. The external communication apparatus 300 is connected to the control panel 133 of the walking training apparatus 100 by, for example, a USB cable, and is also connected for communication to an Internet network 400 as an example of external networks through a wireless communication device 410 which is, for example, a wireless LAN unit.

The server 500 is connected to the Internet network 400 and has a function of accumulating training data received from the external communication apparatus 300. Further, the server 500 has a function of providing accumulated training data according to a request of a terminal 600 connected to the Internet network 400. Thus, a data viewer (e.g., a user) can read and view training data accumulated in the server 500 by operating the terminal 600.

The server 500 also has a function of generating, as a server side definition file, a definition file that defines a mode of uploading when the external communication apparatus 300 transmits the training data to the server 500, and transmitting the definition file to the external communication apparatus 300.

In the above-described walking training system, the walking training apparatus 100 is connected to the Internet network 400 through the external communication apparatus 300 as described above and does not have a communication function of directly connecting to the Internet network 400. That is, the walking training apparatus 100 does not directly output training data to the external network. By interposing the external communication apparatus 300 between the Internet network 400 and the walking training apparatus 100 as described above, it is possible to prevent training data from being leaked from the walking training apparatus 100. The connection between the walking training apparatus 100 and the external communication apparatus 300 is not limited to connection using a USB cable. That is, various communication standards can be adopted as long as they use communication paths that do not go through any external network.

Figure 2:
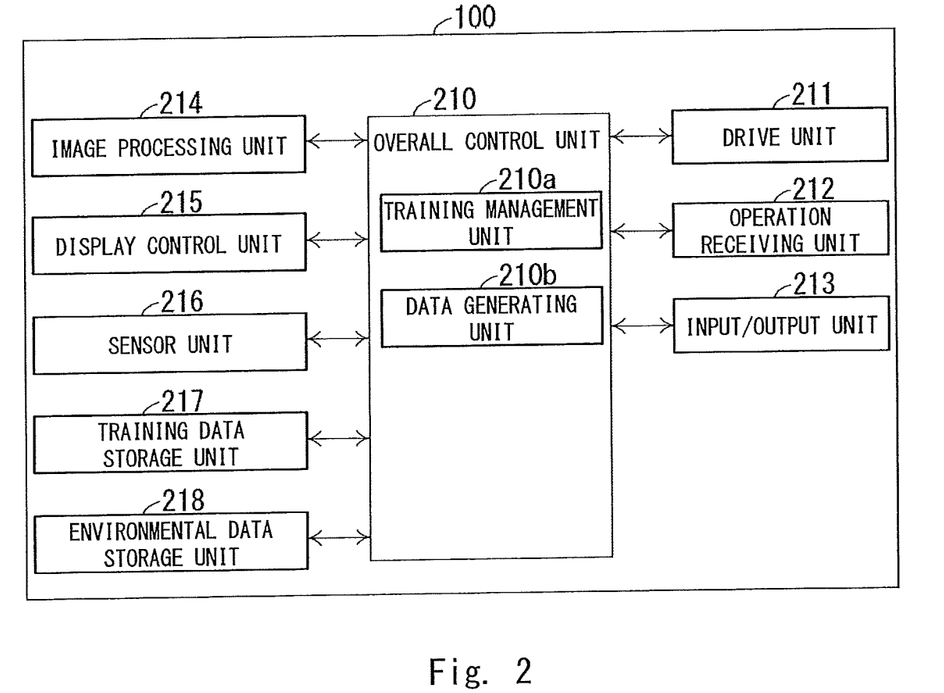
FIG. 2 is a block diagram showing a configuration of the walking training apparatus.

FIG. 2 is a block diagram showing a configuration of the walking training apparatus 100. The overall control unit 210 is, for example, an MPU, and controls the overall operation of the apparatus by executing a control program loaded from the system memory.

A drive unit 211 includes a motor and its drive circuit for each of the treadmill 131, the front pulling unit 135, the rear pulling unit 137, and the walking assistance apparatus 120, which are disposed in a distributed manner. The overall control unit 210 performs drive control by transmitting drive signals to the respective drive units 211. For example, the overall control unit 210 adjusts the running speed of the endless belt 132 according to the set walking speed and turns the motors of the front and rear pulling units 135 and 137 on/off in synchronization with the timing at which the diseased leg is changed from a leg-standing state to a leg-idling state.

An operation receiving unit 212 receives an input operation performed by the trainee 900 or an operator and transmits an operation signal to the overall control unit 210. The trainee 900 or the operator operates operation buttons provided in the apparatus, a remote controller belonging to the apparatus, or the like, which constitutes the operation receiving unit 212, and thereby provides an instruction to start or shut down the walking training apparatus 100, to start a training, enters numerical values for the setting, or selects a menu item.

An input/output unit 213 includes, for example, a USB interface. The input/output unit 213 is a communication interface for connecting to the external communication apparatus 300 and other external devices. The overall control unit 210 communicates with the external devices through the input/output unit 213, receives rewriting and commands of a training program, and outputs the generated training data.

An image processing unit 214 generates image data by image-processing an image signal received from the camera 140 according to an instruction received from the overall control unit 210. Further, the image processing unit 214 can perform a specific image analysis by image-processing an image signal received from the camera 140 according to an instruction received from the overall control unit 210. For example, the image processing unit 214 detects a position of the diseased leg (leg-standing position) in contact with the treadmill 131 by performing an image analysis. Further, the image processing unit 214 can generate image data by performing a trimming or the like in order to adapt image data to the data format of training data. For example, the image processing unit 214 cuts out an area near the foot (hereinafter referred to as a foot area) from the image data when generating moving image data of the moving leg.

A display control unit 215 receives a display signal from the overall control unit 210, generates a display image, and displays the generated image on the training monitor 138. The display control unit 215 displays images showing the progress of the training and real-time video images taken by the camera 140 according to the display signal.

A sensor unit 216 includes various sensors disposed in a distributed manner and their drive circuits. The overall control unit 210 performs sensing control by transmitting a sensing starting signal or an output request signal for each of the sensors to the sensor unit 216. The overall control unit 210 processes received sensor outputs, records the processed data on the training data, performs feedback for the subsequent control, and so on.

The overall control unit 210 also functions as a function performing unit which performs various calculations and controls related to the control. A training management unit 210*a* controls the walking training apparatus 100 according to a training program and successively collects information on the walking training of the trainee 900. A data generating unit 210*b* generates training data in a predetermined format from the information on the walking training collected by the training management unit 210*a*, the state of the apparatus, information attributed to the trainee 900 himself/herself, and so on. Then, the data generating unit 210*b* writes the generated training data in a training data storage unit 217. The overall control unit 210 outputs the training data and environmental data, which will be described later, to the external communication apparatus 300 in response to a power-on of the walking training apparatus 100 or an input operation of the operator input via the operation receiving unit 212.

The training data storage unit 217 stores the training data generated by the data generating unit 210*b* of the overall control unit 210.

Figure 3:
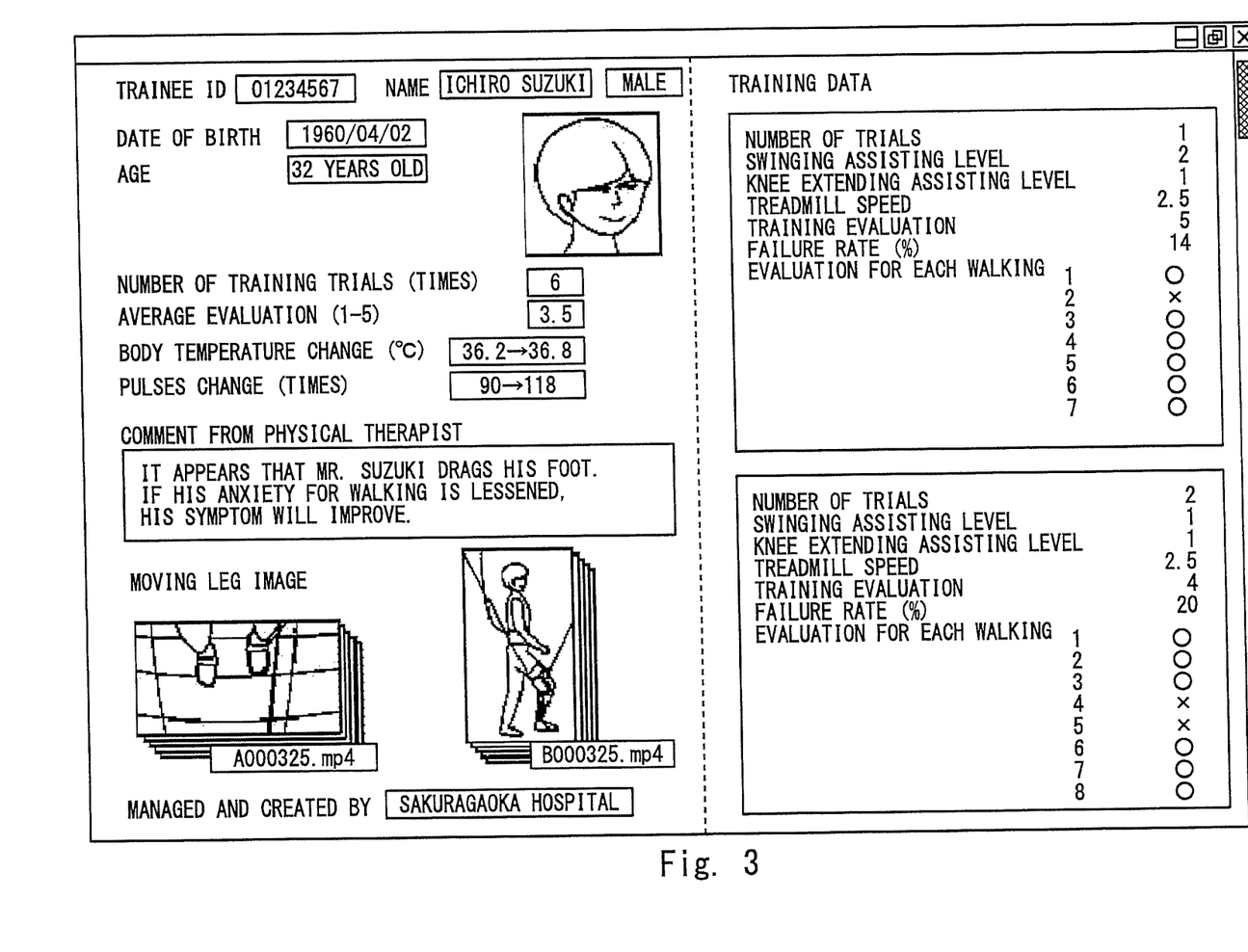
FIG. 3 is a diagram showing a state in which an example of training data is visibly displayed.

The training data will be described below. FIG. 3 is a diagram showing a state in which an example of the training data is visibly displayed. The training data is formed by associating a main body file including the attributed information such as a name of the trainee 900 and a training result of the trainee 900 with a related image file.

As shown in the drawing, when the training data is displayed on a viewing monitor, a viewer who is, for example, a doctor can visually recognize the information attributed to the trainee 900, the training result, the image data, etc. Examples of the attributed information include a trainee ID, a name, a sex, a date of birth, an age, and a face photograph (identification image). These are information for identifying the trainee 900. The identification image may be in a format in which the image data is embedded in the main body file or a format in which link information about a link to the image file is written therein.

Examples of the training result include an average evaluation value of training, vital information such as a pulse change, a comment of a physical therapist who has accompanied the trainee 900 in the training, a moving image of the moving leg, and detailed data of each training trial. As for the moving image in the example of the drawing, foot moving images obtained by trimming the images captured by the camera 140 and side moving images captured by a lateral camera (not shown in FIG. 1) are acquired as the link information. For example, the foot moving image is linked to a moving image file named A000325.mp4. When images are captured in each of a plurality of training trials, the foot moving image is linked to a plurality of the moving image files. In addition to the above data, a name of the physical therapist who has accompanied the trainee 900 in the training and a management creator of the training data are also stored as parts of the training data.

Returning to FIG. 2, an environmental data storage unit 218 stores the environmental data, which will be described later.

Figure 4:
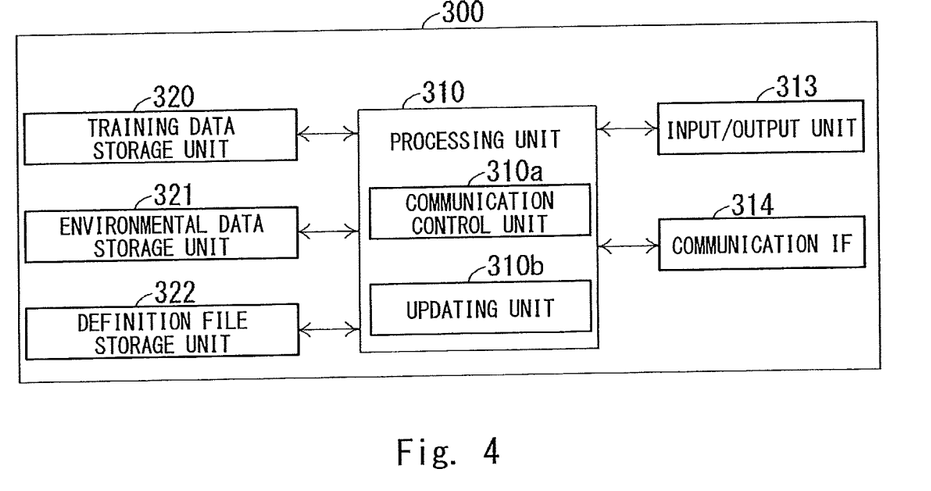
FIG. 4 is a block diagram showing a configuration of an external communication apparatus.

FIG. 4 is a block diagram showing a configuration of the external communication apparatus 300. A processing unit 310 is, for example, an MPU, and performs processes which the external communication apparatus 300 is in charge of by executing a control program loaded from the system memory.

An input/output unit 313 includes, for example, a USB interface, and is a communication interface for connecting for communication with the walking training apparatus 100. The processing unit 310 communicates with the walking training apparatus 100 through the input/output unit 313. Further, the processing unit 310 receives training data and environmental data output from the walking training apparatus 100 and transmits various request signals to the walking training apparatus 100.

A communication IF 314 includes, for example, a wireless LAN interface, and is a communication interface for connecting the Internet network 400. In the example shown in FIG. 1, the communication IF 314 connects to the Internet network 400 by using a wireless communication device 410 as an access point.

A training data storage unit 320 is, for example, a HDD, and stores training data. The processing unit 310 writes training data received from the walking training apparatus 100 through the input/output unit 213 into the training data storage unit 320.

An environmental data storage unit 321 is, for example, an HDD. The environmental data storage unit 321 stores the environmental data. The environmental data includes information related to a system operating state of the medical apparatus 700, information related to a system error message of the medical apparatus 700, sensor data of the medical apparatus 700, information related to an OS operation log of the medical apparatus 700, and information related to system backup of the medical apparatus 700.

The training data and the environmental data are specific examples of the medical apparatus side data.

Figure 5:
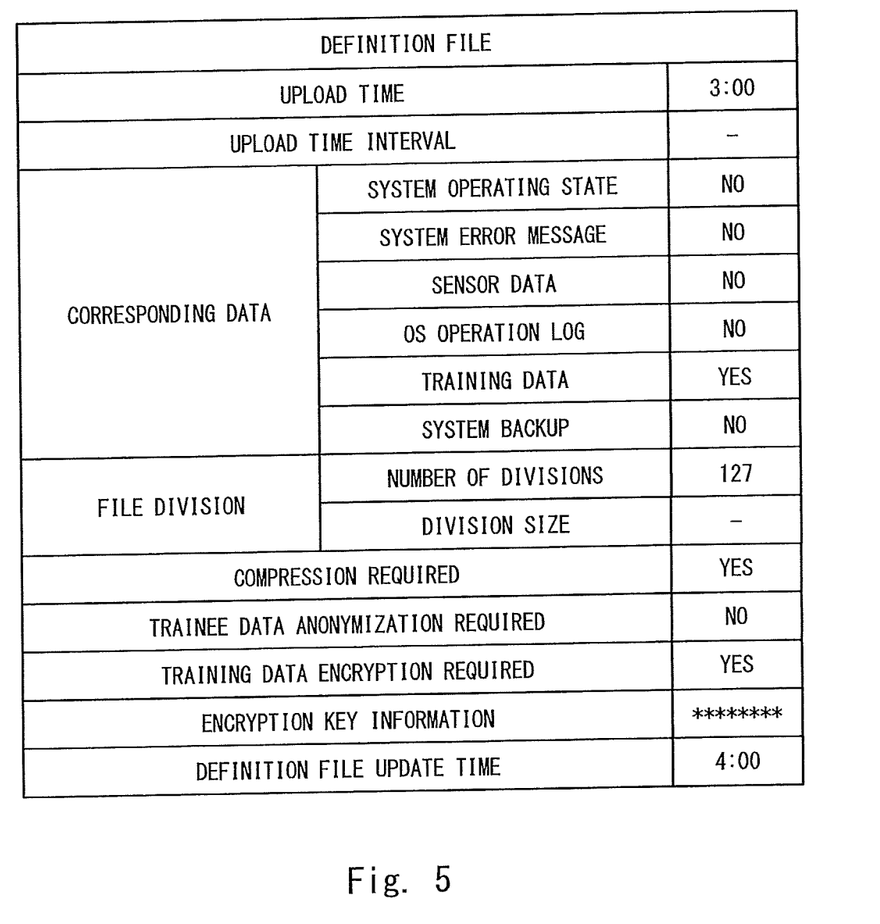
FIG. 5 is a diagram showing a file structure of a definition file.

A definition file storage unit 322 is, for example, an HDD. The definition file storage unit 322 stores the definition file as a client side definition file. The definition file defines a mode of uploading for the external communication apparatus 300 to upload the medical apparatus side data to the server. FIG. 5 is a diagram showing a file structure of the definition file. As shown in FIG. 5, the definition file includes data listed below.

Upload time: The upload time indicates time at which the external communication apparatus 300 uploads the medical apparatus side data to the server 500. The upload time is set, for example, between 2:00 and 4:00, so as not to disturb an operation of the walking training apparatus 100.

Upload time interval: The upload time interval indicates a time interval at which the external communication apparatus 300 uploads the medical apparatus side data to the server 500.

Corresponding data: The corresponding data indicates a specific content of the medical apparatus side data uploaded by the external communication apparatus 300 to the server 500. The corresponding data includes at least one of the training data and the environmental data.

File division: The file division indicates the number of divisions when the external communication apparatus 300 divides the medical apparatus side data and uploads the divided medical apparatus side data to the server 500, and a division size corresponding to a maximum value of one divided file size.

Trainee data anonymization required: The trainee data anonymization required indicates whether the trainee data needs to be anonymized when the external communication apparatus 300 uploads the training data to the server 500.

Training data encryption required: The training data encryption required indicates whether the trainee data needs to be encrypted when the external communication apparatus 300 uploads the training data to the server 500.

Encryption key information: The encryption key information indicates information related to an encryption key to encrypt the training data when the external communication apparatus 300 uploads the training data to the server 500.

Definition file update time: The definition file update time indicates time at which the external communication apparatus 300 accesses the server 500 and downloads the latest definition file stored in the server 500 to thereby update the client side definition file of the external communication apparatus 300. The definition file update time is set, for example, between 2:00 to 4:00 so as not to disturb the operation of the walking training apparatus 100.

The environmental data storage unit 321 and the definition file storage unit 322 are specific examples of a medical apparatus side data storage unit.

The processing unit 310 includes a communication control unit 310a and an updating unit 310b. The communication control unit 310a has a function of controlling communication with the server 500. The updating unit 310b has a function of updating the client side definition file. The communication control unit 310a communicates with the server 500 via the communication IF 314 and downloads the server side definition file from the server 500. The updating unit 310b updates the client side definition file with the server side definition file. Then, the communication control unit 310a transmits the medical apparatus side data to the server 500 based on the client side definition file.

Figure 6:
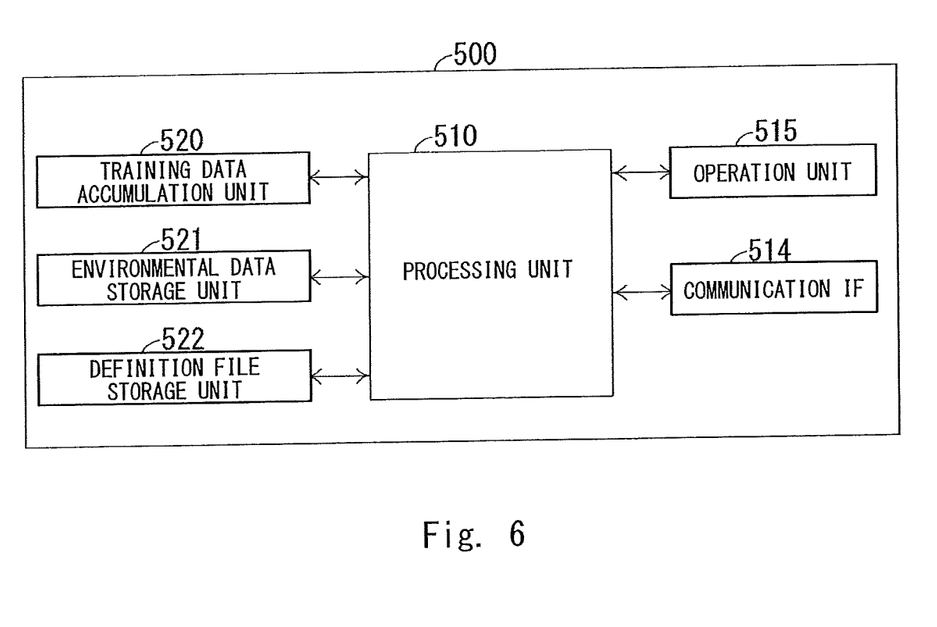
FIG. 6 is a block diagram showing a configuration of a server.

FIG. 6 is a block diagram showing a configuration of the server 500. A processing unit 510 is, for example, an MPU. The processing unit 510 executes control on the server 500 by executing a control program read from the system memory.

A communication IF 514 includes, for example, a wired LAN interface. The communication IF 514 is a communication interface for communicatively connecting to the Internet network 400. The processing unit 510 receives the medical apparatus side data from the external communication apparatus 300 via the communication IF 514. The processing unit 510 generates the server side definition file in response to operation processing of the terminal 600.

An operation unit 515 is an input device such as a keyboard and a mouse connected to a server main body. A system administrator operates the operation unit 515 when he/she creates the server side definition file. The processing unit 510 receives the operation processing of the operation unit 515 and generates the server side definition file.

A data accumulation unit 520 is, for example, an HDD. The data accumulation unit 520 stores the training data. The processing unit 510 writes the training data received from the external communication apparatus 300 via the communication IF 514 in the data accumulation unit 520. Further, the processing unit 510 reads the training data requested by the terminal 600 from the data accumulation unit 520 via the communication IF 514 and transmits it to the terminal 600.

An environmental data storage unit 521 is, for example, an HDD. The environmental data storage unit 521 stores the environmental data. The processing unit 510 writes the environmental data received from the external communication apparatus 300 via the communication IF 514 in the environmental data storage unit 521. Further, the processing unit 510 reads the environmental data requested by the terminal 600 via the communication IF 514 from the data accumulation unit 520 and transmits it to the terminal 600.

A definition file storage unit 522 is, for example, an HDD. The definition file storage unit 522 stores the server side definition file. The processing unit 510 writes the server side definition file created by the system administrator in the definition file storage unit 522 via the operation unit 515. The processing unit 510 also writes the server side definition file received from the terminal 600 in the definition file storage unit 522 via the communication IF 514.

In this way, the content of the server side definition file stored in the definition file storage unit 522 of the server 500 can be freely changed by the system administrator and the user of the terminal 600. Thus, the system administrator and the user of the terminal 600 can freely change the client side definition file stored in the definition file storage unit 322 of the external communication apparatus 300 by appropriately changing the server side definition file stored in the definition file storage unit 522 of the server 500.

Figure 7:
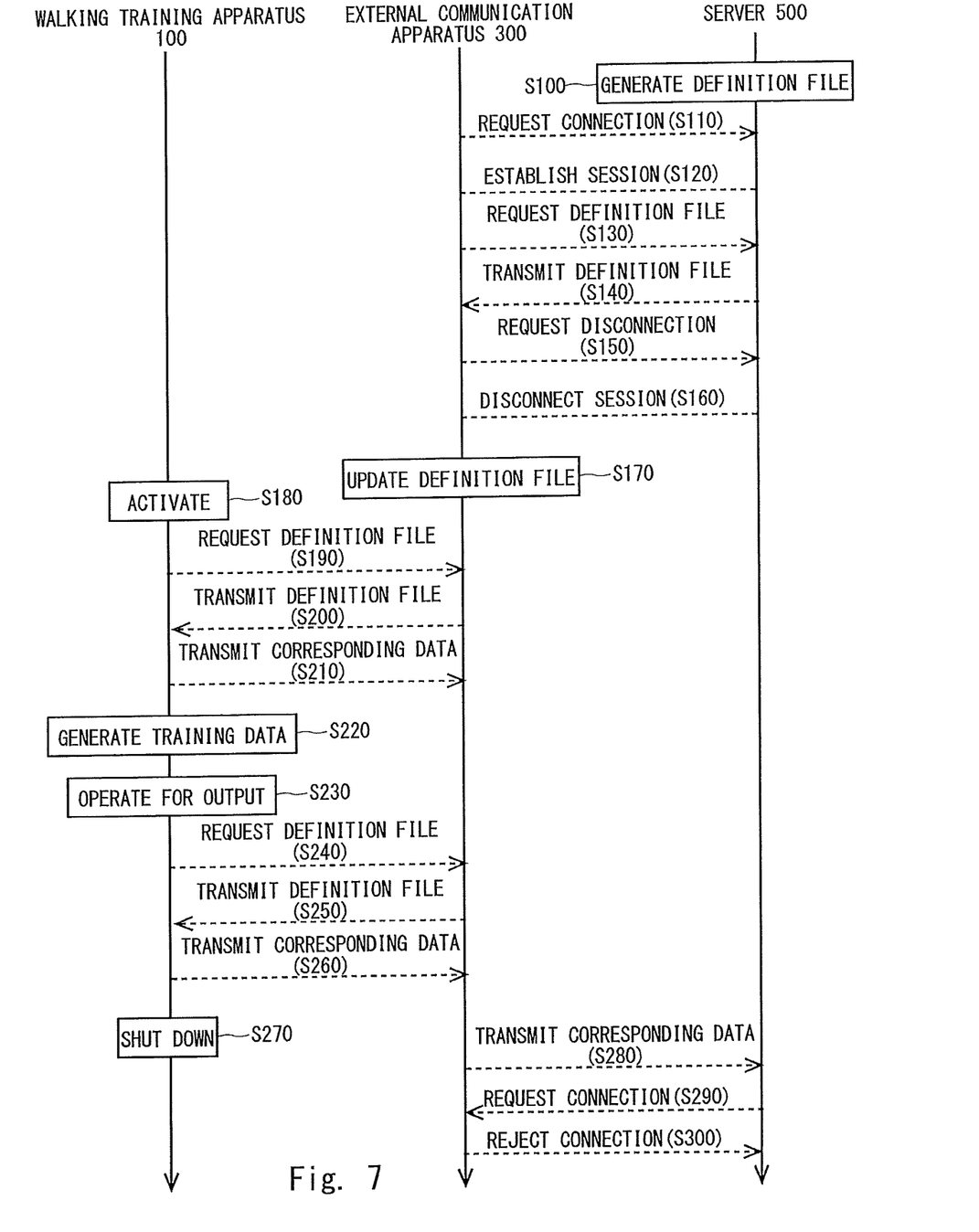
FIG. 7 is a processing flowchart of the walking training apparatus, the external communication apparatus, and a server.

Next, a processing flow of a data communication program for controlling each of the walking training apparatus 100, the external communication apparatus 300, and the server 500 will be described. FIG. 7 is a processing flowchart of the walking training apparatus, the external communication apparatus, and the server. The downward arrow on the left side shows a process progress of the walking training apparatus 100, the downward arrow at the center shows a process progress of the external communication apparatus 300, and the downward arrow on the right shows a process progress of the server 500. The respective processes connected by dotted arrows in the horizontal direction represent processing executed at substantially the same time. In the flow of FIG. 7, suppose that the walking training apparatus 100 is not activated, the training data and the environmental data have already been stored in the training data storage unit 320 and the environmental data storage unit 321 of the walking training apparatus 100.

S100:

First, when the system administrator of the server 500 operates the operation unit 515, or the user of the terminal 600 operates the terminal 600, the processing unit 510 generates the server side definition file and writes the generated server side definition file in the definition file storage unit 522.

S110-S120:

Next, the communication control unit 310a of the external communication apparatus 300 requests a communication connection to the server 500 at the definition file update time defined in the client side definition file (S110). Then, a communication connection (session) is established between the communication control unit 310a of the external communication apparatus 300 and the server 500 (S120).

S130-S140:

Next, the communication control unit 310a of the external communication apparatus 300 requests the server 500 for the server side definition file (S130). When the server 500 is requested by the external communication apparatus 300 for the server side definition file, it reads the server side definition file from the definition file storage unit 522 and transmits it to the external communication apparatus 300 (S140). That is, the communication control unit 310a of the external communication apparatus 300 downloads the server side definition file from the server 500.

S150-S160:

Next, the communication control unit 310a of the external communication apparatus 300 requests a communication disconnection to the server 500 (S150). Then, the communication connection (session) between the external communication apparatus 300 and the server 500 is disconnected (S160).

S170:

Next, the updating unit 310b of the external communication apparatus 300 updates the client side definition file stored in the definition file storage unit 322 with the server side definition file received from the server 500. That is, the updating unit 310b of the external communication apparatus 300 updates the client side definition file by overwriting the client side definition file stored in the definition file storage unit 322 with the server side definition file. Then, the client side definition file stored in the definition file storage unit 322 of the external communication apparatus 300 becomes the latest one generated by the server 500. The updating unit 310b of the external communication apparatus 300 compares the server side definition file received from the server 500 with the client side definition file stored in the definition file storage unit 322. When there is no difference between them, the updating unit 310b may omit the above updating.

S180:

Next, the operator of the walking training apparatus 100 activates the walking training apparatus 100 when a walking training facility opens.

S190-S210:

Next, the overall control unit 210 of the walking training apparatus 100 requests the external communication apparatus 300 for the definition file in response to the activation of the walking training apparatus 100 (S190). When the external communication apparatus 300 is requested for the definition file from the walking training apparatus 100, it transmits the client side definition file stored in the definition file storage unit 322 to the walking training apparatus 100 (S200). Then, the walking training apparatus 100 transmits the corresponding data to the external communication apparatus 300 in accordance with the client side definition file received from the external communication apparatus 300 (S210). The external communication apparatus 300 writes the corresponding data received from the walking training apparatus 100 in the training data storage unit 320 and the environmental data storage unit 321.

S220:

Next, when the training management unit 210a completes a series of training trials on the walking training apparatus 100, the data generating unit 210b adjusts the training data, the information attributed to the trainee 900, and the like in accordance with a predetermined format to generate the training data.

S230-S260:

Next, when the operator instructs the walking training apparatus 100 to write the training data in the external communication apparatus 300 via the operation receiving unit 212 (S230), the overall control unit 210 of the walking training apparatus 100 requests the external communication apparatus 300 for the definition file in response to an operation of the operator via the operation receiving unit 212 (S240). When the external communication apparatus 300 is requested for the definition file by the walking training apparatus 100, it transmits the client side definition file stored in the definition file storage unit 322 to the walking training apparatus 100 (S250). Then, the walking training apparatus 100 transmits the corresponding data to the external communication apparatus 300 in accordance with the client side definition file received from the external communication apparatus 300 (S260). The external communication apparatus 300 writes the corresponding data received from the walking training apparatus 100 in the training data storage unit 320 and the environmental data storage unit 321.

S270:

Next, the operator of the walking training apparatus 100 shuts down the walking training apparatus 100 when the walking training facility closes.

S280:

Next, the communication control unit 310a of the external communication apparatus 300 requests a communication connection to the server 500 at the upload time defined in the client side definition file and establishes a communication connection between the communication control unit 310a of the external communication apparatus 300 and the server 500. Then, the communication control unit 310a of the external communication apparatus 300 transmits the corresponding data to the server 500 in a specified scheme according to the mode of the uploading defined in the client side definition file (S280). The server 500 writes the corresponding data received from the external communication apparatus 300 in the data accumulation unit 520 and the environmental data storage unit 521. In this way, the server 500 can acquire desired data from the medical apparatus 700 in a desired scheme as intended by the system administrator of the server 500 or the user of the terminal 600.

S290-S300:

Note that the server 500 cannot forcibly rewrite the client side definition file stored in the definition file storage unit 322 of the external communication apparatus 300. That is, when the server 500 requests a communication connection to the external communication apparatus 300 (S290), the communication control unit 310a of the external communication apparatus 300 rejects the request for a communication connection from the server 500 (S300). In short, when the external communication apparatus 300 is a client, pushing is prohibited and only fetching is permitted while the server side definition file is downloaded from the server 500 to the external communication apparatus 300. This effectively reduces the risk that the definition file storage unit 322 of the external communication apparatus 300 may be rewritten without a permission by an external server other than an authorized server.

The preferred embodiment of the present disclosure has been described above. The above embodiment has the following features.

A medical information system includes the server 500 and the medical apparatus 700 (the walking training apparatus 100 and the external communication apparatus 300). The medical apparatus 700 uploads the medical apparatus side data (the training data and the environmental data) to the server 500. The server 500 includes the server side definition file storage unit 322 configured to store a server side definition file that defines a mode of the uploading. The medical apparatus 700 includes the medical apparatus side data storage unit (the training data storage unit 320 and the environmental data storage unit 321) configured to store the medical apparatus side data, the client side definition file storage unit 322 configured to store the client side definition file that defines the mode of the uploading, the communication control unit 310a configured to control communication with the server 500, and the updating unit 310b configured to update the client side definition file. The communication control unit 310a of the external communication apparatus 300 requests a communication connection to the server 500. When the communication connection is established with the server 500, the communication control unit 310a acquires the server side definition file from the server 500. The updating unit 310b of the external communication apparatus 300 updates the client side definition file with the server side definition file acquired by the communication control unit 310a. The communication control unit 310a of the external communication apparatus 300 is configured to upload the medical apparatus side data to the server 500 based on the client side definition file. Further, the communication control unit 310a of the external communication apparatus 300 is configured to reject the connection request from the server 500. With the above configuration, the definition file can be freely updated by the authorized server 500, and the definition file can be prohibited from being updated by an external server other than the authorized server 500.

Preferably, the medical apparatus side data includes medical data of the subject of the medical apparatus 700. With the above configuration, the medical data is effectively prevented from leaking.

Preferably, the client side definition file defines at least one of time of executing the uploading (the upload time in FIG. 5), the time interval for executing the uploading (the upload time interval in FIG. 5), a type of the data to be uploaded (the corresponding data in FIG. 5). With the above configuration, the client side definition file specifically defining the mode of the uploading is achieved.

Further, the medical apparatus 700 (the walking training apparatus 100 and the external communication apparatus 300) that uploads the medical apparatus side data to the server 500 based on the definition file that defines the mode of the uploading includes the medical apparatus side storage unit (the training data storage unit 320 and the environmental data storage unit 321) that stores the definition file, the definition file storage unit 322 that stores the definition file, the communication control unit 310a that controls communication with the server 500, and the updating unit 310b that updates the definition file. The communication control unit 310a requests a communication connection to the server 500. When a communication connection with the server 500 is established, the communication control unit 310a acquires the definition file stored in the server 500. The updating unit 310b updates the definition file stored in the definition file storage unit 322 with the definition file acquired by the communication control unit 310a. The communication control unit 310a is configured to upload the medical apparatus side data to the server 500 based on the definition file. Further, the communication control unit 310a is configured to reject the connection request from the server 500. With the above configuration, the definition file can be freely updated by the authorized server 500, and the definition file can be prohibited from being updated by an external server other than the authorized server 500.

The data communication method of the medical apparatus 700 in which the medical apparatus 700 uploads medical apparatus side data to the server 500 based on the definition file that defines the mode of the uploading includes a step (Steps S110-S160 in FIG. 7) of requesting, by the medical apparatus 700, a communication connection to the server 500, and when the communication connection is established with the server 500, acquiring, by the medical apparatus 700, the definition file stored in the server 500, a step (S170 in FIG. 7) of updating, by the medical apparatus 700, the definition file stored in the medical apparatus 700 with the acquired definition file, and a step (S280 in FIG. 7) of uploading, by the medical apparatus, the medical apparatus side data to the server 500 based on the definition file stored in the medical apparatus 700. Then, the medical apparatus 700 rejects the connection request from the server 500 (Steps S290-S300 in FIG. 7). With the above method, the definition file can be freely updated by the authorized server 500, and the definition file can be prohibited from being updated by an external server other than the authorized server 500.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A medical information system comprising:
    a server; and
    a medical apparatus configured to upload medical apparatus side data to the server, wherein
    the server comprises a server side definition file storage configured to store a server side definition file that defines a mode of the uploading, and
    the medical apparatus comprises:
        a medical apparatus side data storage configured to store the medical apparatus side data;
        a client side definition file storage configured to store a client side definition file that defines the mode of the uploading;
        a medical device; and
        an external communication apparatus that includes a processor configured to:
            request a first communication connection to the server,
            when the first communication connection is established with the server, acquire the server side definition file from the server,
            disconnect the first communication connection with the server after the server side definition file is acquired,
            update the client side definition file stored in the client side definition file storage of the medical apparatus with the acquired server side definition file,
            after the client side definition file is updated and before reception of medical apparatus side data,
                receive a request from the medical device for the updated client side definition file,
                in response to reception of the request from the medical device, transmit the updated client side definition file to the medical device, and
                receive the medical apparatus side data from the medical device in accordance with the updated client side definition file,
            after reception of the medical apparatus side data from the medical device, request a second communication connection to the server,
            when the second communication connection to the server is established, upload the medical apparatus side data to the server based on the client side definition file, and
            disconnect the second communication connection with the server after the medical apparatus side data is uploaded to the server,
            after the client side definition file is updated and the first communication connection or the second communication connection with the server is disconnected, reject a connection request from a second server for a communication connection between the second server and the medical apparatus, wherein the second server is an unauthorized server.

2. The medical information system according to claim 1, wherein the medical apparatus side data includes medical data of a subject of the medical apparatus.

3. The medical information system according to claim 1, wherein the client side definition file defines at least one of a time for executing the uploading, a time interval for executing the uploading, and a type of data to be uploaded.

4. A medical apparatus for uploading medical apparatus side data to a server based on a client side definition file that defines a mode of the uploading, the medical apparatus comprising:
    a medical apparatus side data storage configured to store the medical apparatus side data;
    a definition file storage configured to store the client side definition file;
    a medical device; and
    an external communication apparatus that includes a processor configured to:
        request a first communication connection to the server,
        when the first communication connection is established with the server, acquire a server side definition file stored in the server,
        disconnect the first communication connection with the server after the server side definition file is acquired,
        update the client side definition file stored in the definition file storage of the medical apparatus with the acquired server side definition file,
        after the client side definition file is updated and before reception of medical apparatus side data,
            receive a request from the medical device for the updated client side definition file,
            in response to reception of the request from the medical device, transmit the updated client side definition file to the medical device, and receive the medical apparatus side data from the medical device in accordance with the updated client side definition file, after reception of the medical apparatus side data from the medical device, request a second communication connection to the server, when the second communication connection to the server is established, upload the medical apparatus side data to the server based on the updated client side definition file stored in the definition file storage, disconnect the second communication connection with the server after the medical apparatus side data is uploaded to the server, and after the client side definition file is updated and the first communication connection or the second communication connection with the server is disconnected, reject a connection request from a second server for a communication connection between the second server and the medical apparatus, wherein the second server is an unauthorized server.

5. A data communication method of a medical apparatus in which the medical apparatus uploads medical apparatus side data to a server based on a client side definition file that defines a mode of the uploading, the medical apparatus including a medical device and an external communication apparatus that includes a processor, the data communication method comprising:

requesting, by the processor, a first communication connection to the server;

when the first communication connection is established with the server, acquiring, by the processor, a server side definition file stored in the server;

disconnecting, by the processor, the first communication connection with the server after the server side definition file is acquired;

updating, by the processor, the client side definition file stored in the medical apparatus with the acquired server side definition file;

after the client side definition file is updated and before reception of medical apparatus side data,
 receiving, by the processor, a request from the medical device for the updated client side definition file,
 in response to reception of the request from the medical device, transmitting, by the processor, the updated client side definition file to the medical device, and
 receiving, by the processor, the medical apparatus side data from the medical device in accordance with the updated client side definition file;

after reception of the medical apparatus side data from the medical device, requesting, by the processor, a second communication connection to the server;

when the second communication connection to the server is established, uploading, by the processor, the medical apparatus side data to the server based on the updated client side definition file stored in the medical apparatus;

disconnecting, by the processor, the second communication connection with the server after the medical apparatus side data is uploaded to the server; and rejecting, by the processor after the client side definition file is updated and the first communication connection or the second communication connection with the server is disconnected, a connection request from a second server for a communication connection between the second server and the medical apparatus, wherein the second server is an unauthorized server.

6. A non-transitory computer readable medium storing a program for causing a computer to execute the data communication method according to claim 5.

7. The medical information system according to claim 1, wherein the external communication apparatus and the medical device are physically separate.

\* \* \* \* \*